United States Patent
Hoey et al.

(10) Patent No.: US 9,982,211 B2
(45) Date of Patent: May 29, 2018

(54) COMPOSITION AND METHOD OF FORMING THE SAME

(71) Applicant: BASF SE, Ludwigshafen (DE)

(72) Inventors: Michael Dennis Hoey, Maplewood, NJ (US); Eugene Scanlon, Mamaroneck, NY (US); Frederick Mensah, White Plains, NY (US); Douglas S. Brown, Tuxedo Park, NY (US); Alfred Karl Jung, Carmel, NY (US); Shaun Robert Seibel, Yorktown Heights, NY (US); Patrick Daniel Hasenhuetl, Chatham, NJ (US); Ralf Lorenz Schmitt, Riehen (CH)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/101,704

(22) PCT Filed: Dec. 4, 2014

(86) PCT No.: PCT/US2014/068604
§ 371 (c)(1),
(2) Date: Jun. 3, 2016

(87) PCT Pub. No.: WO2015/085083
PCT Pub. Date: Jun. 11, 2015

(65) Prior Publication Data
US 2016/0304801 A1    Oct. 20, 2016

Related U.S. Application Data

(60) Provisional application No. 61/912,698, filed on Dec. 6, 2013.

(51) Int. Cl.
| | | |
|---|---|---|
| *C10M 159/12* | (2006.01) | |
| *C07F 9/06* | (2006.01) | |
| *C10M 137/10* | (2006.01) | |
| *C07F 9/165* | (2006.01) | |

(52) U.S. Cl.
CPC .......... *C10M 159/123* (2013.01); *C07F 9/06* (2013.01); *C07F 9/1651* (2013.01); *C10M 137/105* (2013.01); *C10M 2223/043* (2013.01); *C10M 2223/047* (2013.01); *C10N 2220/021* (2013.01); *C10N 2230/06* (2013.01); *C10N 2230/08* (2013.01); *C10N 2230/50* (2013.01); *C10N 2230/64* (2013.01); *C10N 2240/08* (2013.01); *C10N 2240/10* (2013.01); *C10N 2240/12* (2013.01); *C10N 2240/14* (2013.01); *C10N 2240/40* (2013.01)

(58) Field of Classification Search
CPC .................. C10M 2223/043; C10M 2223/047
USPC ................................................ 508/428, 430
See application file for complete search history.

(56) References Cited

U.S. PATENT DOCUMENTS

| | | | |
|---|---|---|---|
| 3,637,499 A | 1/1972 | Pollak | |
| 4,333,841 A | 6/1982 | Schmidt et al. | |
| 4,575,431 A | 3/1986 | Salentine | |
| 5,362,419 A | 11/1994 | Zinke et al. | |
| 5,922,657 A | 7/1999 | Camenzind et al. | |
| 7,919,440 B2 | 4/2011 | Zakarian et al. | |
| 9,040,470 B2* | 5/2015 | Yagishita | C10M 141/10 508/364 |
| 2004/0053794 A1* | 3/2004 | Baba | C10M 137/00 508/430 |
| 2004/0147410 A1 | 7/2004 | Milner et al. | |
| 2004/0214733 A1* | 10/2004 | Baba | C10M 141/10 508/430 |
| 2004/0242437 A1 | 12/2004 | Reyes-Gavlian et al. | |
| 2004/0259743 A1* | 12/2004 | Butke | C10M 141/10 508/273 |
| 2008/0269085 A1 | 10/2008 | Haire et al. | |

(Continued)

FOREIGN PATENT DOCUMENTS

| | | |
|---|---|---|
| EP | 0 098 809 A2 | 1/1984 |
| EP | 1006173 A1 | 6/2000 |
| WO | WO 8808874 A2 | 11/1988 |

OTHER PUBLICATIONS

International Search Report PCT/US2014/068604 dated Mar. 31, 2015, 4 pages.

(Continued)

*Primary Examiner* — Ellen M McAvoy
(74) *Attorney, Agent, or Firm* — Lowenstein Sandler LLP

(57) ABSTRACT

A composition comprises the reaction product of a dithiophosphate derivative and an amine. The reaction product is present in the composition in an amount of at least about 25 wt. %. The composition may include additional components. A method of forming the composition comprises the step of combining the dithiophosphate derivative and the amine to form the composition. A method of increasing thermal stability of a dithiophosphate derivative comprises the step of combining the dithiophosphate derivative and an amine. The dithiophosphate derivative can decompose to form hydrogen sulfide (H2S). However, the amine substantially prevents thermal decomposition of the dithiophosphate derivative. An example of the dithiophosphate derivative is 3-(di-isobutoxy-thiophosphorylsulfanyl)-2-methyl-propanoic acid. An example of the amine is ditridecyl amine. The composition can be used for a variety of applications. For example, the composition can be used as an antiwear compound/additive in lubricants, metalworking fluids, hydraulic fluids, etc.

13 Claims, No Drawings

(56) References Cited

U.S. PATENT DOCUMENTS

2010/0009878 A1 1/2010 Baba et al.
2010/0009881 A1 1/2010 Ryan et al.
2015/0337231 A1* 11/2015 Sato .................... C10M 141/10
 508/430

OTHER PUBLICATIONS

English language abstract and machine-assisted English translation for EP 0 098 809 extracted from espacenet.com database on Aug. 14, 2017, 13 pages.

* cited by examiner

COMPOSITION AND METHOD OF FORMING THE SAME

CROSS-REFERENCE TO RELATED APPLICATIONS

This application is the National Stage of International Patent Application No. PCT/US2014/068604, filed on Dec. 4, 2014, which claims priority to and all the advantages of U.S. Provisional Patent Application No. 61/912,698, filed on Dec. 6, 2013, the content of which is incorporated herein by reference.

FIELD OF THE INVENTION

The present invention generally relates to a composition comprising the reaction product of a dithiophosphate derivative and an amine, to a method of forming the composition, and to a method of increasing thermal stability of a dithiophosphate derivative that can decompose to form hydrogen sulfide ($H_2S$). The composition may be used as an antiwear additive.

DESCRIPTION OF THE RELATED ART

Certain materials will form hydrogen sulfide ($H_2S$) if they are heated. Thermal decomposition of the material is generally to blame. Thermal decomposition of the material can occur during shipping, handling, and/or storage of the material. Thermal decomposition can occur when a vessel (e.g. a drum) containing the material is stored on a loading dock, or in a truck, railcar, warehouse, etc. Hot and sunny climates are especially problematic. When the vessel is eventually opened, workers can be exposed to escaping $H_2S$ that can be irritating to toxic.

Materials such as dithiophosphate derivatives can be used as antiwear additives. If certain dithiophosphate derivatives are heated to ~60° C. or higher, $H_2S$ is formed. Therefore, workers can be exposed to $H_2S$ while handling dithiophosphate derivatives and during manufacture of compositions that utilize dithiophosphate derivatives, such as during manufacture of lubricants, metalworking fluids, hydraulic fluids, etc. Therefore, air handlers, safety masks, and/or respirators should be utilized during such handling and manufacturing. Unfortunately, it is difficult to enforce safety/hygiene measures on an ongoing basis.

$H_2S$ exposure is covered under Occupational Safety & Health Administration (OSHA) standards. Worker exposure limits are generally based on the particular type of industry. For "General", the standards are set forth in 29 CFR 1910.1000, TABLE Z-2, "Toxic and hazardous substances". Exposures must not exceed 20 parts per million (ppm) (ceiling), subject to an exception. If no other measurable exposure occurs during an 8-hour work shift, exposures may exceed 20 ppm, but not more than 50 ppm (peak), for a single time period up to 10 minutes. For "Construction", the standards are set forth in 29 CFR 1926.55, Appendix A, "Gases, vapors, fumes, dusts, and mists". An exposure limit of 10 ppm (15 mg/m$^3$) time-weighted average (TWA) is set. For "Shipyard", the standards are set forth in 29 CFR 1915.1000, Table Z, "Air contaminants". An exposure limit of 10 ppm TWA is set.

Similarly, the National Institute for Occupational Safety and Health (NIOSH) has a Recommended Exposure Limit (REL) of 10 ppm, 10-minute ceiling. The $H_2S$ concentration considered immediately dangerous to life and health (IDLH) is 100 ppm. The American Conference of Industrial Hygienists (ACGIH®) recommends a threshold limit value (TLV®) of 1 ppm as an 8-hour TWA and a short-term exposure limit of 5 ppm.

Attempts have been made to reduce $H_2S$ exposure in various industries. For example, conventional methods for removing $H_2S$ from fuels include reaction with iron oxide, hydrodesulfurization, and filtration via impregnated active carbon. Unfortunately, these methods can be both time consuming and expensive. In addition, these methods are purely remedial in nature. In other words, these methods can only address existing $H_2S$. Therefore, any $H_2S$ that may be subsequently formed is unaccounted for and poses an ongoing threat.

In view of the foregoing, there remains an opportunity to provide compositions having improved thermal stability, as well as an opportunity to provide methods of manufacturing such compositions. There also remains an opportunity to provide improved methods of reducing $H_2S$ formation and exposure.

SUMMARY OF THE INVENTION AND ADVANTAGES

Disclosed is a composition. The composition comprises the reaction product of a dithiophosphate derivative and an amine. The reaction product is present in the composition in an amount of at least about 25 wt. %. Also disclosed is a method of forming the composition. The method comprises the step of combining the dithiophosphate derivative and the amine to form the composition. Yet also disclosed is a method of increasing thermal stability of a dithiophosphate derivative. The method comprises the step of combining the dithiophosphate derivative and the amine. The dithiophosphate derivative can decompose to form hydrogen sulfide ($H_2S$). However, the amine substantially prevents thermal decomposition of the dithiophosphate derivative.

It has surprisingly been found that combining dithiophosphate derivatives with certain compounds increases thermal stability of the dithiophosphate derivatives. Amines have been found to be especially useful in this regard. Improvement in thermal stability dramatically reduces $H_2S$ formation when the dithiophosphate derivatives are exposed to typical decomposition conditions. Therefore, $H_2S$ exposure is also reduced or completely prevented, especially in instances where the dithiophosphate derivative is exposed to instances of heating that would have previously caused thermal decomposition.

DETAILED DESCRIPTION OF THE INVENTION

Disclosed is a composition. Also disclosed is a method of forming the composition. The composition comprises the reaction product of a dithiophosphate derivative and an amine. In certain embodiments, the composition consists essentially of the reaction product of the dithiophosphate derivative and the amine. In further embodiments, the composition consists of the reaction product of the dithiophosphate derivative and the amine.

Various types of dithiophosphate derivatives can be utilized to form the reaction product. In many embodiments, the dithiophosphate derivative is of the following general formula:

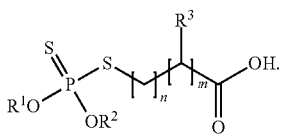

(I)

Typically, $R^1$ and $R^2$ independently of one another are $C_3$-$C_{18}$ alkyl, $C_5$-$C_{12}$ cycloalkyl, $C_5$-$C_6$ cycloalkylmethyl, $C_9$-$C_{10}$ bicycloalkylmethyl, $C_9$-$C_{10}$ tricycloalkylmethyl, phenyl, or $C_7$-$C_{24}$ alkylphenyl. In further embodiments, $R^1$ and $R^2$ independently of one another are $C_3$-$C_{18}$ alkyl, $C_5$-$C_6$ cycloalkyl, or $C_7$-$C_{18}$ alkylphenyl. In an alternate embodiment, $R^1$ and $R^2$ together are $(CH_3)_2C(CH_2)_2$, i.e., $R^1$ and $R^2$ define a cyclic structure. The carbon chain lengths can be of any subrange of the foregoing ranges. Specific examples of $R^1$ and $R^2$ independently of one another are i-propyl, i-butyl, or 2-ethylhexyl.

Where $R^1$ and $R^2$ in formula (I) are $C_3$-$C_{18}$ alkyl, they can independently of one another be branched or unbranched radicals. Examples of such radicals are propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, and 1-methylundecyl.

Where $R^1$ and $R^2$ in formula (I) are $C_5$-$C_{12}$ cycloalkyl, they can independently of one another be, e.g., cyclopentyl, cyclohexyl, cycloheptyl, cyclooctyl, or cyclododecyl. Where $R^1$ and $R^2$ in formula (I) are $C_5$-$C_6$ cycloalkylmethyl, they can independently of one another be, e.g., cyclopentylmethyl or cyclohexylmethyl. An example of a suitable $C_9$-$C_{10}$ bicycloalkylmethyl is decalinylmethyl.

Where $R^1$ and $R^2$ in formula (I) are $C_9$-$C_{10}$ tricycloalkylmethyl, they can independently of one another be, e.g., of the following general formula:

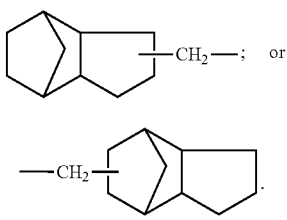

Examples of suitable alkylphenyls are methylphenyl, dimethylphenyl, trimethylphenyl, ethylphenyl, isopropylphenyl, t-butylphenyl, di-t-butylphenyl, and 2,6-di-t-butyl-4-methylphenyl. $R^1$ and $R^2$ can be the same as or different from one another.

In formula (I), $R^3$ is hydrogen (H) or methyl ($CH_3$). The sum of n+m is at least 1. Typically, the sum of n+m is from 1 to 25, 1 to 20, 1 to 15, 1 to 10, 1 to 5, 1 to 2, or any integer between 1 and 25. In these embodiments, it is possible that one of n and m is zero (0), e.g. where $R^3$ is hydrogen.

The dithiophosphate derivative can be of various molecular weights. In certain embodiments, the dithiophosphate derivative has a number average molecular weight (Mn) of less than about 3,000, less than about 2,750, less than about 2,500, less than about 2,250, less than about 2,000, less than about 1,750, less than about 1,500, less than about 1,250, less than about 1,000, less than about 750, or less than about 500.

In a specific embodiment, each of $R^1$ and $R^2$ is isobutyl, $R^3$ is methyl, n is 1, and m is 1. In another specific embodiment, each of $R^1$ and $R^2$ is isobutyl, $R^3$ is hydrogen, n is 1, and m is 1.

By "derivative", it is generally meant that the dithiophosphate derivative is derived from a precursor compound, e.g. a dithiophosphoric acid. The instant disclosure is not limited to a particular method of forming the dithiophosphate derivative. Various embodiments of the dithiophosphate derivative can be prepared in accordance with the following general reaction scheme:

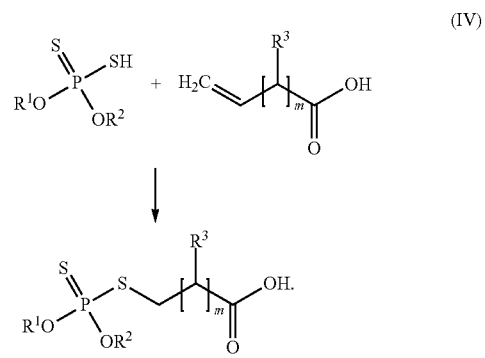

(IV)

In certain embodiments, the dithiophosphate derivative is classified as a β-dithiophosphorylated propionic acid. The synthesis of β-dithiophosphorylated propionic acid by addition of dithiophosphoric acid onto acrylic or methacrylic acid is described, e.g., in U.S. Pat. No. 5,362,419 to Zinke et al. (e.g. in Examples 1 through 11), and in U.S. Pat. No. 5,922,657 to Camenzind et al., which also describes the synthesis of some β-dithiophosphorylated propionic acids (e.g. in Examples 1 through 3). The disclosures of U.S. Pat. Nos. 5,362,419 and 5,922,657 are incorporated herein by reference in their entirety.

Examples of suitable dithiophosphate derivatives are commercially available from BASF Corporation of Florham Park, N.J., under the trademark IRGALUBE®. A specific example of a suitable dithiophosphate derivative is IRGALUBE® 353, which is a dialkyl dithiophosphate ester. Another specific example of a suitable dithiophosphate derivative is IRGALUBE® 63. In specific embodiments, the dithiophosphate derivative is 3-(di-isobutoxy-thiophosphorylsulfanyl)-2-methyl-propanoic acid (CAS #268567-32-4). Combinations of different dithiophosphate derivatives can be utilized to form the reaction product.

Various types of amines can be utilized to form the reaction product. The amine typically has at least one amine functional group. The amine functional group is reactive with the dithiophosphate derivative Amines having one, two, three, or more amine functional groups may be used. The amine functional group(s) can be primary, secondary, tertiary, or combinations thereof.

The amine may be classified as a monoamine, a diamine, a triamine, or a polyamine. The amine can be an aliphatic amine, a cycloaliphatic amine, an aromatic amine, or a cycloaromatic amine. In certain embodiments, the amine is an aliphatic or cycloaliphatic amine. In further embodiments, the amine is a secondary aliphatic amine. In a specific embodiment, the amine is ditridecyl amine (CAS #101012-

97-9; which may also be referred to as "DTDA"). In other specific embodiments, the amine is a primary $C_8$ to $C_{22}$, primary $C_{12}$ to $C_{18}$, or primary $C_{16}$ to $C_{18}$, alkyl amine. In these embodiments, the primary alkyl amine can have any number of carbon atoms between 8 and 22.

Further examples of suitable amines include ethylene diamine, toluene diamine, 1,3-diaminpropane, putrescine, cadaverine, hexamethylenediamine, 1,2-diaminopropane, diphenylethylenediamine, diaminocyclohexane, xylylenediamines, phenylenediamine, benzidine, spermidine, spermine, toluene diamine, aminobenzylamines, polyether diamines, and combinations thereof. Yet further examples include diethylene diamine, polyethylene diamine (e.g. having a Mn of from about 200 to about 2,000), propylene diamine, dipropylene diamine, polypropylene diamine (e.g. having a Mn of from about 200 to about 3,000), butylene diamine, dibutylene diamine, polybutylene diamine (e.g. having a Mn of from about 200 to about 4,000), and combinations thereof.

In various embodiments, the amine can comprise a polyester polyamine, a polyether polyamine, a polyether/ester polyamine, or combinations thereof. Furthermore, the amine may be selected from aliphatic polyamines, cycloaliphatic polyamines, aromatic polyamines, heterocyclic polyamines, and combinations thereof. Examples of suitable amines include glycol-initiated polyamines, glycerine-initiated polyamines, sucrose-initiated polyamines, sucrose/glycerine-initiated polyamines, trimethylolpropane-initiated polyamines, and combinations thereof.

Further examples of suitable amines include divalent and higher polyvalent primary or secondary, aliphatic, aralipathic, cycloaliphatic or aromatic amines. Specific examples include 4-aminobenzylamines, 4,4'-diaminodicyclohexylmethane, phenylene diamines, etc. Polyamines such as diethylenetriamine, triethylenetetramine, diethylenepropylamine, N-(2-hydroxyethyl)diethylenetriamine, N,N'-di(2-hydroxyethyl)diethylenetriamine, m-phenylenediamine, methylenedianiline, aminoethyl piperazine, 4,4-diaminodiphenyl sulfone, benzyldimethylamine, dicyandiamide, and 2-methylimidazole, and triethylamine, can also be utilized.

Suitable aromatic amines such as a diaminodiphenylsulfone, a methylenedianiline such as 4,4'-methylenedianiline, a diaminodiphenylether, benzidine, 4,4'-thiodianiline, 4-methoxy-6-m-phenylenediamine, 2,6-diaminopyridine, 2,4-toluenediamine, and dianisidine can be utilized. Further examples include alicyclic amines, such as menthane diamine and heterocyclic amines, such as pyridine. Aliphatic amines such as secondary alkylamines can be utilized.

Further suitable amines include the isomeric phenylene diamines, 4,4'-diaminobenzophenone, bis(4-amino)diphenyl ether, and 2,2-bis(4-aminophenyl)propane. Other examples of suitable amines include alcohol amines, such as ethanol amine and diethanol amine Further examples of suitable amines include m-phenylenediamine, p-phenylenediamine, 4,4'-diaminodiphenyl ether, 3,4'-diaminodiphenyl ether, 4,4'-diaminodiphenylsulfone, 3,3'-diaminodiphenylsulfone, 2,2'-ditrifluoromethyl-4,4'-diaminobiphenyl, 9,9-bis(4-aminophenyl)fluorene, 9,9-bis(4-mino-3-methylphenyl)fluorene, bis[4-(4-aminophenoxy)phenyl]sulfone, bis[4-(3-aminophenoxy)phenyl]sulfone, 2,2-bis[4-(4-aminophenoxy)phenyl]propane, 3-(methylamino)propylamine, and 2,2-bis(4-aminophenyl)hexafluoropropane. Other examples include alkyl amines, propyl amine, isobutyl amine, alkyleneoxide amines, etc.

Examples of suitable amines are commercially available from Infineum USA L.P. of Linden, N.J., under the trademark INFINEUM®. A specific example of a suitable amine is INFINEUM® C9268, which is a polyamine dispersant. Combinations of different amines can be utilized to form the reaction product.

The amine can be of various molecular weights. In certain embodiments, the amine has a Mn less than about 3,000, less than about 2,750, less than about 2,500, less than about 2,250, less than about 2,000, less than about 1,750, less than about 1,500, less than about 1,250, less than about 1,000, less than about 750, or less than about 500. Without being bound or limited to any particular theory, it is thought that amines having "higher" molecular weights, e.g. a Mn of about 2,000, about 2,250, or higher, can be less effective for certain purposes of the instant disclosure relative to amines having "lower" molecular weights, e.g. a Mn of about 100 to about 1,000, or about 250 to about 750. Specifically, it is thought that higher molecular weights can be detrimental for certain applications of the composition, such as when the composition is utilized as an antiwear additive. In general, it is thought that starting at about 2000, as the Mn of the amine increases, antiwear effectiveness of the antiwear additive decreases. Similarly, it is thought that amines having numerous amine functional groups, e.g. polyamines having 5, 10, or more amine functional groups, can be less effective for certain purposes of the instant disclosure relative to amines having fewer amine functional groups, e.g. 1 to 3 amine functional groups. Specifically, it is thought that too many amine functional groups on one molecule of amine can bind up too many molecules of the dithiophosphate derivative. Therefore, the composition could lose antiwear effectiveness when utilized as an antiwear additive.

The reaction product is present in the composition in an amount of at least about 25 wt. %. In further embodiments, the reaction product is present in the composition in an amount of at least about 30, at least about 35, at least about 40, at least about 45, at least about 50, at least about 55, at least about 60, at least about 65, at least about 70, at least about 75, at least about 80, at least about 85, at least about 90, at least about 95, at least about 99, wt. %, or any subrange in between about 25 and about 99 wt. %. In a specific embodiment, the reaction product is present in the composition in an amount of 100 wt. %, i.e., the reaction product is the composition.

In various embodiments, the composition can include one or more supplemental components in addition to the reaction product. In certain embodiments, the composition comprises "free" dithiophosphate derivative, i.e., an amount of dithiophosphate derivative that has not reacted with the amine. This situation can arise when a molar excess of the dithiophosphate derivative is utilized to form the reaction product. An additional amount of dithiophosphate derivative can also be added post-reaction. If present, the free dithiophosphate derivative may be the same as or different from the dithiophosphate derivative utilized to form the reaction product.

If present in the composition, the free dithiophosphate derivative can make up the remainder of the composition. For example, the free dithiophosphate derivative can be present in the composition in an amount of from about 1 to about 75 wt. %, or any subrange in between. Including free dithiophosphate derivative in the composition is optional.

Other supplemental components that may be present in the composition, in addition or alternate to the free dithiophosphate derivative, include customary additives, such as solvents, base oils, moisture scavengers, desiccants, antioxidants, metal passivators, rust inhibitors, dispersants, viscosity index improvers, pour point depressants, other antiwear additives, and combinations thereof. Specific examples of some of these components are described in U.S. Pat. Nos. 5,362,419 and 5,922,657, as well as in U.S. Pat. App. Pub. No. 2004/0242437 to Reyes-Gavlian et al., the disclosure of which is also incorporated herein by reference in its entirety.

If utilized, the additive(s) can make up the remainder of the composition. For example, the additive(s) can be present in the composition in an amount of from about 1 to about 75 wt. %, or any subrange in between. Generally, if the composition also includes free dithiophosphate derivative, the amount of additive(s) is skewed toward lower wt. % ranges, e.g. about 0.001 to about 20, about 0.01 to about 10, about 0.1 to about 5, or about 1 to about 2.5, wt. %, with the remainder generally being the reaction product and free dithiophosphate derivative. In embodiments where the composition includes one or more additives, the composition can be referred to as an additive package or additive composition. Including additive(s) in the composition is optional.

The method of forming the composition comprises the step of combining the dithiophosphate derivative and the amine to form the composition. When the dithiophosphate derivative and the amine are combined (or contacted), the reaction product begins to form. There can be instances where the reaction product is the composition (i.e., 100 wt. %), or instances where the reaction product is but one component of the composition. In the latter embodiments, the method can further comprise the step of combining (or adding) the supplemental component(s), e.g. an additive, to further form the composition. The components can be mixed to facilitate reaction and formation of the composition. Without limitation, conventional reaction vessels, mixers, blenders, etc. can be utilized to form the composition.

The method is not limited to any particular order of addition of the components. Additions can be all-at-once or step-wise. Reaction between the dithiophosphate derivative and the amine is exothermic. To prevent formation of undesirable byproducts, e.g. hydrogen sulfide ($H_2S$), excess heat may be removed during and/or after the reaction. Proactive means can also be utilized. Without limitation, various temperature control means can be utilized, such as controlled addition of the reactants, jacketed reactors, heatsinks, heat-exchangers, etc. Typically, the reaction is maintained below the decomposition temperature of the dithiophosphate derivative, e.g. below about 60° C., and more typically the reaction is maintained at or about room temperature (~23±3° C.).

The dithiophosphate derivative and the amine can be provided via various means. Typically, the components are in the form of raw materials. In other words, the components are not already part of an end application, e.g. as mere additives in a lubricant or similar composition. For example, the dithiophosphate derivative can be provided via a storage vessel (e.g. a 55-gallon drum), and fed into a reaction vessel. The amine can be provided in a similar manner and fed into the reaction vessel. After reaction between the components is at (or near) completion, the reaction vessel can be emptied of the composition. Optionally, the supplemental component(s) can be added to the reaction vessel to further form the composition. This can be done prior to, during, and/or after reaction of the dithiophosphate derivative and the amine. If utilized, the supplemental component(s) is typically added after the reaction is at (or near) completion. However, it is possible that certain supplemental components can be useful as heat-sinks, such that they can be added prior to and/or during the reaction to maintain the temperature of the reaction vessel during formation of the composition.

One of the reaction components can simply be added to the other. For example, a portion of the dithiophosphate derivative in a 55-gallon drum can be removed to make room for adding the amine thereto, or vice versa. Alternatively, the dithiophosphate derivative can be drummed in a manner that leaves sufficient space for later adding the amine thereto, or vice versa. Once addition to the drum is complete, the contents of the drum can be mixed to facilitate formation of the composition. Optionally, the supplemental component(s) can also be added to the drum to further form the composition.

In many embodiments, the reaction product can be referred to as an amine salt. In specific embodiments, the reaction product can be referred to as a substituted-ammonium carboxylate salt. An example of the latter is when the dithiophosphate derivative is of formula (I), i.e., where the dithiophosphate derivative includes a carboxyl functional (COOH) group. Typically, the method does not include a purposeful heating step or a purposeful dehydration step, as this can result in formation of undesirable byproducts, e.g. $H_2S$, and/or formation of water and amide. Water can be detrimental for certain end applications of the composition, and can also influence further formation of $H_2S$.

The dithiophosphate derivative and the amine can be reacted in various amounts to form the reaction product. Based on the number of functional groups imparted by each of the reactants, the dithiophosphate derivative and the amine can be utilized in a 1:1 stoichiometric ratio. Alternatively, the dithiophosphate derivative can be utilized in a stoichiometric excess relative to the amine. Conversely, the amine can be utilized in a stoichiometric excess relative to the dithiophosphate derivative. Such situations may also be referred to as over-indexing or under-indexing the reaction, with an index of 1.0 (or 100) indicating that there is a stoichiometric amount of respective functional groups present to react with each other 1:1 (e.g. a COOH group for every amine group). Indices of 1.0, 1:1, or 100 may also be referred to as an equimolar amount. The index may be from 0.25 to 2.0, 0.5 to 1.5, 0.9 to 1.1, 0.95 to 1.05, or 1.0, or any number in between.

In various embodiments, the amine is utilized in an amount that is sufficient to meet various safety standards for $H_2S$ exposure. $H_2S$ exposure is covered under Occupational Safety & Health Administration (OSHA) standards. Worker exposure limits are generally based on the particular type of industry. For "General", the standards are set forth in 29 CFR 1910.1000, TABLE Z-2, "Toxic and hazardous substances". Exposures must not exceed 20 parts per million (ppm) (ceiling), subject to an exception. If no other measurable exposure occurs during an 8-hour work shift, exposures may exceed 20 ppm, but not more than 50 ppm (peak), for a single time period up to 10 minutes. For "Construction", the standards are set forth in 29 CFR 1926.55, Appendix A, "Gases, vapors, fumes, dusts, and mists". An exposure limit of 10 ppm (15 mg/m$^3$) time-weighted average (TWA) is set. For "Shipyard", the standards are set forth in 29 CFR 1915.1000, Table Z, "Air contaminants". An exposure limit of 10 ppm TWA is set. These OSHA standards are incorporated herein by reference.

Similarly, the National Institute for Occupational Safety and Health (NIOSH) has a Recommended Exposure Limit (REL) of 10 ppm, 10-minute ceiling. The $H_2S$ concentration considered immediately dangerous to life and health (IDLH) is 100 ppm. The American Conference of Industrial Hygienists (ACGIH®) recommends a threshold limit value (TLV®) of 1 ppm as an 8-hour TWA and a short-term exposure limit of 5 ppm.

In many embodiments, the composition meets OSHA Standards for $H_2S$ exposure. Specifically, immediately after formation of the composition, $H_2S$ exposure from the composition does not exceed 10 ppm (15 mg/m³). In other embodiments, $H_2S$ exposure from the composition does not exceed about 25, about 20, about 15, about 8, about 5, about 2, or about 1, ppm. Such $H_2S$ levels are in the context of the composition after formation. Depending on the $H_2S$ level, the composition may also meet NIOSH recommendations and/or ACGIH® recommendations.

In various embodiments, the "original" composition, which is prepared by simply adding composition to a headspace vial, generates less than about 25, about 20, about 15, about 12, about 11, about 10, about 9, about 8, about 7, about 6, about 5, about 4, about 3, about 2, about 1, or about 0.5, ppm $H_2S$ when tested via gas chromatography (GC) in accordance with ASTM D5504 and the testing procedure set forth in the examples below. Further, in these embodiments, the "aged" composition, which is prepared by adding composition to a headspace vial and aging the headspace vial with the composition therein for 72 hours at 60° C., generates less than about 25, about 20, about 15, about 12, about 11, about 10, about 9, about 8, about 7, about 6, about 5, about 4, about 3, about 2, about 1, or about 0.5, ppm when tested via gas chromatography (GC) in accordance with ASTM D5504 and the testing procedure set forth in the examples below.

To start, "neat" samples are prepared by adding composition to headspace vials and aging each headspace vial with the composition therein for 1 hour at 60° C., and "aged" samples are prepared by adding composition to headspace vials and aging each headspace vial with the composition therein for 72 hours at 60° C.

$H_2S$ exposure may be higher than 10 ppm (or other levels above) if the composition is subjected to decomposition conditions after formation. Such conditions are undesirable, and are generally associated with heating the composition to a temperature that is approaching at, or above, a thermal decomposition temperature of the dithiophosphate derivative(s) utilized to form the composition. For example, the dithiophosphate derivative (prior to reaction with the amine) can have a decomposition temperature that is at least about 60° C. The decomposition temperature may be higher or lower than 60° C. depending on the particular dithiophosphate derivative(s) utilized to form the composition.

Surprisingly, it has been found that utilizing the amine(s) substantially prevents thermal decomposition of the dithiophosphate derivative(s). Specifically, prior to reaction with the amine, the dithiophosphate derivative can decompose to form $H_2S$ when subjected to a temperature approaching at, or above, a thermal decomposition temperature of the dithiophosphate derivative.

By "substantially", it is generally meant that formation of $H_2S$ is reduced relative to formation of $H_2S$ associated with the same dithiophosphate derivative, but while in an unreacted state, under the same heating conditions. Typically, formation of $H_2S$ is reduced by at least 10%, by at least 25%, by at least 50%, by at least 75%, or more. Under certain conditions, formation of $H_2S$ is completely avoided.

Referring to the dithiophosphate derivative of formula (I), heating the dithiophosphate derivative, e.g. to a temperature of at least about 60° C., can cause the sulfur-carbon bond to break. This is similar to if the reaction scheme (IV) were to be reversed; however, the reactants would not be the same. Once the sulfur-carbon bond is broken, it is thought that the molecular portion having the COOH group drives the further breakdown of additional molecules of the dithiophosphate derivative. The remaining molecular portion having the sulfur atoms is then free to further break down to form $H_2S$. The presence of a donor (e.g. water) can accelerate formation of $H_2S$.

When the amine is combined with the dithiophosphate derivative, thermal stability of the dithiophosphate derivative is generally increased. Specifically, without being bound or limited to any particular theory, it is thought the amine reacts with the dithiophosphate derivative, e.g. reacts with the COOH group, to stabilize the dithiophosphate derivative. Stability of the dithiophosphate derivative is increased such that the sulfur-carbon bond is less prone to break while the composition is subjected to heating. On one hand, it is thought that the amine increases the decomposition temperature of the dithiophosphate derivative. It is also thought that the amine structurally stabilizes the dithiophosphate derivative while in the form of the reaction product, e.g. amine salt, to prevent breakage of the sulfur-carbon bond.

Preventing formation of $H_2S$ via the instant disclosure is a proactive approach, relative to merely addressing $H_2S$ after its formation, i.e., relative to remedial approaches. An added benefit of the instant disclosure is increased robustness relative to conventional compositions. For example, while $H_2S$ can be removed from a conventional composition, e.g. via impregnated active carbon filtration, there is still the potential for additional $H_2S$ to form should the conventional composition be subjected to thermal decomposition conditions. In contrast, this potential is greatly reduced or completely avoided with the instant disclosure.

The instant disclosure also provides a method of increasing thermal stability of the dithiophosphate derivative. The method comprises the step combining the dithiophosphate derivative and the amine. As described above, the dithiophosphate derivative can decompose to form $H_2S$. However, the amine substantially prevents thermal decomposition of the dithiophosphate derivative.

This method can be carried out as like the method of formation above. For example, the components are generally provided in an independent state, e.g. as raw material, rather than already being incorporated into an end application, e.g. as mere additives in a lubricant, in customary additive amounts. In various embodiments, the dithiophosphate derivative is provided in a first part and the amine is provided in a second part. Typically, the first part consists essentially of, or consists of, the dithiophosphate derivative. Similarly, the second part consists essentially of, or consists of, the amine. The first and second parts are combined to form the composition. This method can also be classified as a method of reducing $H_2S$ exposure.

In alternate embodiments of the instant disclosure, the amine is replaced in whole or in part by another compound. The compound can be selected from the group of peptides, epoxides, Michael acceptors (e.g. dibutyl maleate), alkyl halides, alkyl succinic anhydrides, and combinations thereof. The amine is typically utilized to form the reaction product.

INDUSTRIAL APPLICABILITY

The composition is useful for a variety of end applications, and is not limited to any particular use. For example, the composition can be used as an antiwear additive, such as an antiwear additive for use in a lubricant, metalworking fluid, or hydraulic fluid. In certain embodiments, the composition may be referred to as an ashless antiwear composition or ashless antiwear compound.

It is thought that potential benefits provided by, or attributable to, the composition include, but are not limited to, reduced H$_2$S formation, reduced H$_2$S exposure (or emission), increased thermal stability (e.g. at about or greater than 60, 80, 100, 120, 140, 160, or 180,° C., or any temperature between 60 and 180° C.), increased compatibility (e.g. in/with oil and/or seals), passage of high temperature L-37 axle testing (e.g. testing for 24 hours at 163° C.), passage of thermal durability testing (e.g. 800 hour cycle axle testing at 130° C.), and combinations thereof.

If utilized as an antiwear additive, the composition can be used in customary amounts, such as from about 0.001 to about 20, about 0.001 to about 15, about 0.01 to about 10, about 0.01 to about 7.5, about 0.1 to about 5, about 0.1 to about 2.5, or about 0.1 to about 1, wt. %, or in any wt. % in between, each based on the total weight of the end composition (e.g. a lubricant, metalworking fluid, or hydraulic fluid). Other end compositions may utilize the composition of the instant disclosure in a lower or higher amount.

Examples of end applications in which the composition of the instant disclosure can be utilized are described in the incorporated references above. Additional examples of lubricants, in which the composition of the instant disclosure can be utilized, are described immediately below. In these lubricants, the composition of the instant disclosure is simply referred to as the "antiwear additive".

The antiwear additive can be present in the lubricant in various amounts. In various embodiments, the antiwear additive is present in an amount of from about 0.001 to about 20, about 0.001 to about 15, about 0.01 to about 10, about 0.01 to about 7.5, about 0.1 to about 5, about 0.1 to about 2.5, or about 0.1 to about 1, wt. %, or in any wt. % in between, each based on 100 parts by weight of the lubricant.

Typically, the lubricant further comprises a base oil in addition to the antiwear additive. In certain embodiments, the base oil is selected from the group of American Petroleum Institute (API) Group I base oils, API Group II base oils, API Group III base oils, API Group IV base oils, API Group V base oils, and combinations thereof. In these embodiments, the base oil is generally classified in accordance with the API Base Oil Interchangeability Guidelines. In other words, the base oil may be further described as one or more of five types of base oils: Group I (sulphur content >0.03 wt. %, and/or <90 wt. % saturates, viscosity index 80-119); Group II (sulphur content less than or equal to 0.03 wt. %, and greater than or equal to 90 wt. % saturates, viscosity index 80-119); Group III (sulphur content less than or equal to 0.03 wt. %, and greater than or equal to 90 wt. % saturates, viscosity index greater than or equal to 120); Group IV (all polyalphaolefins (PAO's)); and Group V (all others not included in Groups I, II, III, or IV).

The base oil may be further defined as a crankcase lubrication oil for spark-ignited and compression ignited internal combustion engines, including automobile and truck engines, two-cycle engines, aviation piston engines, and marine and railroad diesel engines. Alternatively, the base oil can be further defined as an oil to be used in gas engines, stationary power engines, and turbines. The base oil may be further defined as heavy or light duty engine oil. In one embodiment, the base oil is further defined as heavy duty diesel engine oil.

The base oil may be further defined as base stock oil. Alternatively, the base oil may be further defined as a component that is produced by a single manufacturer to the same specifications (independent of feed source or manufacturer's location) that meets the same manufacturer's specification and that is identified by a unique formula, product identification number, or both. The base oil may be manufactured or derived using a variety of different processes including, but not limited to, distillation, solvent refining, hydrogen processing, oligomerization, esterification, and re-refining. Re-refined stock is typically substantially free from materials introduced through manufacturing, contamination, or previous use.

Alternatively, the base oil may be derived from hydrocracking, hydrogenation, hydrofinishing, refined and re-refined oils or mixtures thereof or may include one or more such oils. In one embodiment, the base oil is further defined as an oil of lubricating viscosity such as natural or synthetic oil and/or combinations thereof. Natural oils include, but are not limited to, animal oils and vegetable oils (e.g., castor oil, lard oil) as well as liquid petroleum oils and solvent-treated or acid-treated mineral lubricating oils such as paraffinic, naphthenic or mixed paraffinic-naphthenic oils.

In various other embodiments, the base oil may be further defined as oil derived from coal or shale. Non-limiting examples of suitable oils include hydrocarbon oils such as polymerized and interpolymerized olefins (e.g., polybutylenes, polypropylenes, propylene-isobutylene copolymers, poly(1-hexenes), poly(1-octenes), poly(1-decenes), and mixtures thereof; alkylbenzenes (e.g., dodecylbenzenes, tetradecylbenzenes, dinonylbenzenes, and di(2-ethylhexyl) benzenes); polyphenyls (e.g., biphenyls, terphenyls, and alkylated polyphenyls), alkylated diphenyl ethers and alkylated diphenyl sulfides and the derivatives, analogs, and homologs thereof.

In still other embodiments, the base oil may be further defined as synthetic oil which may include one or more alkylene oxide polymers and interpolymers and derivatives thereof wherein terminal hydroxyl groups are modified by esterification, etherification, or similar reactions. In various embodiments, these synthetic oils are prepared through polymerization of ethylene oxide or propylene oxide to form polyoxyalkylene polymers which can be further reacted to form the oils. For example, alkyl and aryl ethers of these polyoxyalkylene polymers (e.g., methylpolyisopropylene glycol ether having an average molecular weight of 1,000; diphenyl ether of polyethylene glycol having a molecular weight of 500-1,000; and diethyl ether of polypropylene glycol having a molecular weight of 1,000-1,500) and/or mono- and polycarboxylic esters thereof (e.g. acetic acid esters, mixed $C_3$-$C_8$ fatty acid esters, or the $C_{13}$ oxo acid diester of tetraethylene glycol) may also be utilized.

In even further embodiments, the base oil may include esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, and alkenyl malonic acids) with a variety of alcohols (e.g., butyl alcohol, hexyl alcohol, dodecyl alcohol, 2-ethylhexyl alcohol, ethylene glycol, diethylene glycol monoether, and propylene glycol). Specific examples of these esters include, but are not limited to, dibutyl adipate, di(2-ethylhexyl sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and combinations thereof. Esters useful as the base oil or as included in the base oil also include those formed from $C_5$-$C_{12}$ monocarboxylic acids and polyols and polyol ethers such as neopentyl glycol, trimethylolpropane, pentaerythritol, dipentaerythritol, and tripentaerythritol.

The base oil may be alternatively described as refined oil, re-refined oil, unrefined oil, or combinations thereof. Unrefined oils are typically obtained from a natural or synthetic source without further purification treatment. For example, a shale oil obtained directly from retorting operations, petroleum oil obtained directly from distillation, or ester oil obtained directly from an esterification process and used without further treatment, could all be utilized. Refined oils are similar to the unrefined oils except that they typically have undergone purification to improve one or more properties. Many such purification techniques are known to those of skill in the art such as solvent extraction, acid or base extraction, filtration, percolation, and similar purification techniques. Re-refined oils are also known as reclaimed or reprocessed oils and often are additionally processed by techniques directed to removal of spent additives and oil breakdown products.

In various embodiments, the base oil is present in the lubricant in an amount of from about 70 to about 99.9, about 80 to about 99.9, about 90 to about 99.9, about 75 to about 95, about 80 to about 90, or about 85 to about 95, wt. %, each based on 100 parts by weight of the lubricant. Alternatively, the base oil may be present in the lubricant in amounts of greater than about 70, about 75, about 80, about 85, about 90, about 91, about 92, about 93, about 94, about 95, about 96, about 97, about 98, or about 99, wt. %, each based on 100 parts by weight of the lubricant. In various embodiments, the amount of base oil in a fully formulated lubricant (including additives, diluents, and/or carrier oils, etc.) is from about 80 to about 99.5, about 85 to about 96, or about 87 to about 95, wt. %.

In various embodiments, the base oil has a viscosity ranging from about 1 to about 100, about 1 to about 50, about 1 to about 25, or about 1 to about 20, centistokes (cSt), when tested at 100° C. Viscosity of the base oil can be determined by various methods understood in the art. The present invention is not limited to a particular viscosity of the base oil.

The lubricant may additionally include one or more additives to improve various chemical and/or physical properties of the lubricant. Specific examples of the one or more additives include supplemental antiwear additives (i.e., antiwear additives different from that of the instant disclosure), antioxidants, metal deactivators (or passivators), rust inhibitors, viscosity index improvers, pour point depressors, dispersants, detergents, and antifriction additives. Each of the additives may be used alone or in combination. The additive(s) can be used in various amounts, if employed. The lubricant may be formulated with the additional of several auxiliary components to achieve certain performance objectives for use in certain applications. For example, the lubricant may be a rust and oxidation lubricant formulation, a hydraulic lubricant formulation, turbine lubricant oil, and an internal combustion engine lubricant formulation. In alternate embodiments, the lubricant can be completely free of one or more of the additives described herein.

In certain embodiments, the lubricant comprises the antiwear additive, and one or more further additives, but is free of the base oil. In the immediately preceding embodiments, the lubricant may be referred to as a performance additive package. The antiwear additive and further additive(s) can be present in the performance additive package in various amounts described herein. In related embodiments, the performance additive package consists essentially of, or consists of, the antiwear additive and one or more further additives.

If employed, the supplemental antiwear additive can be of various types. In one embodiment, the supplemental antiwear additive is a zinc dialkyl-dithio phosphate (ZDDP). Alternatively, the supplemental antiwear additive may include sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio]propionate, triphenyl thiophosphate (triphenylphosphorothioate), tris(alkylphenyl) phosphorothioate and mixtures thereof (for example tris(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris[isooctyl 2-acetate], derivatives of 2-mercaptobenzothiazole such as 1-[N,N-bis (2-ethylhexyl)aminomethyl]-2-mercapto-1H-1,3-benzothiazole, ethoxycarbonyl-5-octyldithio carbamate, and/or combinations thereof.

If employed, the supplemental antiwear additive can be used in various amounts. In certain embodiments, the supplemental antiwear additive is present in the lubricant in an amount of from about 0.1 to about 20, about 0.5 to about 15, about 1 to about 10, about 5 to about 10, about 5 to about 15, about 5 to about 20, about 0.1 to about 1, about 0.1 to about 0.5, or about 0.1 to about 1.5, wt. %, each based on 100 parts by weight of the lubricant. Alternatively, the supplemental antiwear additive may be present in amounts of less than about 20, less than about 15, less than about 10, less than about 5, less than about 1, less than about 0.5, or less than about 0.1, wt. %, each based on 100 parts by weight of the lubricant.

If employed, the antioxidant can be of various types. Suitable antioxidants include alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol, and combinations thereof.

Further examples of suitable antioxidants includes alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol, and combinations thereof. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate, and combinations thereof, may also be utilized.

Furthermore, hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide, and combinations thereof, may also be used.

It is also contemplated that alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercapto butane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-[3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra-(5-tert-butyl-4-hydroxy-2-methyl phenyl)pentane, and combinations thereof, may be utilized as antioxidants in the lubricant.

O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithiol terephthalate, bis(3,5-di-tert-butyl-4-hydroxybenzyl)sulfide, isooctyl-3,5di-tert-butyl-4-hydroxy benzylmercaptoacetate, and combinations thereof, may also be utilized.

Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate, and combinations thereof, are also suitable for use as antioxidants.

Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1, 3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl 2,4,6-tris(3,5-di-tert-butyl-4-hydroxyphenylethyl)-1,3,5-triazine, 1,3,5-tris(3,5-di-tert-butyl-4-hydroxyphenyl propionyl)-hexahydro-1,3,5-triazine, 1,3,5-tris(3,5-dicyclohexyl-4-hydroxybenzyl) isocyanurate, and combinations thereof, may also be used.

Additional examples of antioxidants include aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl) phenol, and combinations thereof. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid, and combinations thereof, may also be utilized. In addition, acylaminophenols, for example 4-hydroxylauranilide, 4-hydroxystearanilide, octyl N-(3,5-di-tert-butyl-4-hydroxyphenyl)carbamate.

Esters of [3-(3,5-di-tert-butyl-4-hydroxyphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane, and combinations thereof, may also be used. It is further contemplated that esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane, and combinations thereof, may be used.

Additional examples of suitable antioxidants include those that include nitrogen, such as amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3, 5-di-tert-butyl-4-hydroxyphenylpropionyl)hydrazine. Other suitable examples of antioxidants include aminic antioxidants such as N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethyl-butyl)-N-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenyl amine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino methylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(phenylamino)propane, (o-tolyl)biguanide, bis[4-(1', 3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6, 6-tetramethyl piperid-4-yl) sebacate, 2,2,6,6-tetramethylpiperidin-4-one and 2,2,6,6-tetramethyl piperidin-4-ol, and combinations thereof.

Even further examples of suitable antioxidants include aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,1trithiatridecane and 2,2,15,15-tetramethyl-5,12-dihydroxy-3,7,10,14-tetrathiahexadecane, and combinations thereof. Furthermore, sulfurized fatty esters, sulfurized fats and sulfurized olefins, and combinations thereof, may be used.

If employed, the antioxidant can be used in various amounts. In certain embodiments, the antioxidant is present in the lubricant in an amount of from about 0.01 to about 5, about 0.05 to about 4, about 0.1 to about 3, or about 0.5 to about 2, wt. %, each based on 100 parts by weight of the lubricant. Alternatively, the antioxidant may be present in amounts of less than about 5, less than about 4, less than about 3, or less than about 2, wt. %, each based on 100 parts by weight of the lubricant.

If employed, the metal deactivator can be of various types. Suitable metal deactivators include benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl) tolutriazole, and combinations thereof.

Additional examples of suitable metal deactivators include 1,2,4-triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles, imidazole derivatives, for example 4,4'-methylenebis(2-undecyl-5-methylimidazole) and bis[(N-methyl)imidazol-2-yl] carbinol octyl ether, and combinations thereof. Further examples of suitable metal deactivators include sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one, and combinations thereof. Even further examples of metal deactivators include amino compounds, for example salicylidenepropylenediamine, salicylaminoguanidine and salts thereof, and combinations thereof.

If employed, the metal deactivator can be used in various amounts. In certain embodiments, the metal deactivator is present in the lubricant in an amount of from about 0.01 to about 0.1, about 0.05 to about 0.01, or about 0.07 to about 0.1, wt. %, each based on 100 parts by weight of the lubricant. Alternatively, the metal deactivator may be present in amounts of less than about 0.1, less than about 0.7, or less than about 0.5, wt. %, each based on 100 parts by weight of the lubricant.

If employed, the rust inhibitor and/or friction modifier can be of various types. Suitable examples of rust inhibitors and/or friction modifiers include organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-carboxymethyl-1-dodecyl-3-methylglycerol and the amine salts thereof, and combinations thereof. Additional examples include nitrogen-containing compounds, for example, primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy) propan-2-ol, and combinations thereof. Further examples include heterocyclic compounds, for example: substituted imidazolines and oxazolines, and 2-heptadecenyl-1-(2-hydroxyethyl)imidazoline, phosphorus-containing compounds, for example: amine salts of phosphoric acid partial esters or phosphonic acid partial esters, and zinc dialkyldithiophosphates, molybdenum-containing compounds, such as molydbenum dithiocarbamate and other sulphur and phosphorus containing derivatives, sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof, glycerol derivatives, for example: glycerol monooleate, 1-(alkylphenoxy)-3-(2-hydroxyethyl)glycerols, 1-(alkylphenoxy)-3-(2,3-dihydroxypropyl) glycerols and 2-carboxyalkyl-1,3-dialkylglycerols, and combinations thereof.

If employed, the rust inhibitor and/or friction modifier can be used in various amounts. In certain embodiments, the rust inhibitor and/or friction modifier is/are present in the lubricant in an amount of from about 0.01 to about 0.1, about 0.05 to about 0.01, or about 0.07 to about 0.1, wt. %, each based on 100 parts by weight of the lubricant. Alternatively, the rust inhibitor and/or friction modifier may be present in amounts of less than about 0.1, less than about 0.7, or less than about 0.5, wt. %, each based on 100 parts by weight of the lubricant.

If employed, the viscosity index improver (VII) can be of various types. Suitable examples of VIIs include polyacrylates, polymethacrylates, vinylpyrrolidone/methacrylate copolymers, polyvinylpyrrolidones, polybutenes, olefin copolymers, styrene/acrylate copolymers and polyethers, and combinations thereof.

If employed, the VII can be used in various amounts. In certain embodiments, the VII is present in the lubricant in an amount of from about 0.01 to about 25, about 1 to about 20, or about 1 to about 15, wt. %, each based on 100 parts by weight of the lubricant. Alternatively, the VII may be present in amounts upwards of about 25, upwards of about 20, or upwards of about 15, wt. %, each based on 100 parts by weight of the lubricant.

If employed, the pour point depressant can be of various types. Suitable examples of pour point depressants include polymethacrylate and alkylated naphthalene derivatives, and combinations thereof.

If employed, the pour point depressant can be used in various amounts. In certain embodiments, the pour point depressant is present in the lubricant in an amount of from about 0.01 to about 0.1, about 0.05 to about 0.01, or about 0.07 to about 0.1, wt. %, each based on 100 parts by weight of the lubricant. Alternatively, the pour point depressant may be present in amounts of less than about 0.1, less than about 0.7, or less than about 0.5, wt. %, each based on 100 parts by weight of the lubricant.

If employed, the dispersant can be of various types. Suitable examples of dispersants include polybutenylsuccinic amides or -imides, polybutenylphosphonic acid derivatives and basic magnesium, calcium and barium sulfonates and phenolates, succinate esters and alkylphenol amines (Mannich bases), and combinations thereof.

If employed, the dispersant can be used in various amounts. In certain embodiments, the dispersant is present in the lubricant in an amount of from about 0.01 to about 25, about 0.1 to about 20, about 0.5 to about 15, about 1 to about 12, or about 2.5 to about 9, wt. %, each based on 100 parts by weight of the lubricant. Alternatively, the dispersant may be present in amounts upwards of about 25, upwards of about 20, upwards of about 15, or upwards of about 12, wt. %, each based on 100 parts by weight of the lubricant.

If employed, the detergent can be of various types. Suitable examples of detergents include overbased or neutral metal sulphonates, phenates and salicylates, and combinations thereof.

If employed, the detergent can be used in various amounts. In certain embodiments, the detergent is present in the lubricant in an amount of from about 0.01 to about 5, about 0.1 to about 4, about 0.5 to about 3, or about 1 to about 3, wt. %, each based on 100 parts by weight of the lubricant. Alternatively, the detergent may be present in amounts of less than about 5, less than about 4, less than about 3, less than about 2, or less than about 1, wt. %, each based on 100 parts by weight of the lubricant.

In various embodiments, the lubricant is substantially free of water, e.g. the lubricant includes less than about 5, less than about 4, less than about 3, less than about 2, less than about 1, less than about 0.5, or less than about 0.1, wt. % of water. Alternatively, the lubricant may be completely free of water.

Some of the compounds described above may interact in the lubricant, so the components of the lubricant in final form may be different from those components that are initially added or combined together. Some products formed thereby, including products formed upon employing the lubricant in its intended use, are not easily described or describable. Nevertheless, all such modifications, reaction products, and products formed upon employing the lubricant in its intended use, are expressly contemplated and hereby included herein. Various embodiments include one or more of the modification, reaction products, and products formed from employing the lubricant, as described above.

A method of lubricating a system comprising a fluoropolymer seal is also provided. The method comprises contacting the fluoropolymer seal with the lubricant described above. The system may further comprise an internal combustion engine. Alternatively, the system may further comprise any combustion engine or application that utilizes a lubricant in contact with a fluoropolymer seal, which may also be referred to as a fluoroelastomer seal.

The following examples, illustrating the composition and method of the instant disclosure, are intended to illustrate and not to limit the present invention.

EXAMPLES

Examples of compositions are formulated. Example compositions 1A and 1B are comparative compositions. Example composition 2A, 2B, 3A, and 3B are invention compositions. The compositions are formed by combining and mixing the respective components, and are evaluated using various test methods described below. Each of the test methods are incorporated herein by reference. Additional details are described and illustrated in Tables I through IV below.

TABLE I

| Conestoga Pump Test | Example No. | | |
|---|---|---|---|
| (ASTM D7043) | 1A | 2A | 3A |
| Rings | 20.3 | 25.5 | 82 |
| Vanes | 1.6 | 0.7 | 5.7 |
| Total weight loss* | 21.9 | 26.2 | 87.7 |
| *comment | Pass | Pass | Fail |

The composition of Example 1 consists of a dithiophosphate derivative of formula (I) above, where each of $R^1$ and $R^2$ is isobutyl, $R^3$ is hydrogen, n is 1, and m is 1. Said another way, the composition is "free" (or unreacted) dithiophosphate derivative. The dithiophosphate derivative is generally classified as an antiwear compound, and is commercially available from BASF Corporation. No additional components have been added.

The composition of Example 2 consists of the dithiophosphate derivative of Example 1 that has been neutralized with an amine, specifically with ditridecyl amine. Said another way, the dithiophosphate derivative and the amine have been reacted in an equimolar amount to form the composition. No additional components have been added.

The composition of Example 3 consists of the dithiophosphate derivative of Example 1 that has been neutralized with another amine, specifically with a polyamine polyisobutene (PIB) dispersant. Said another way, the dithiophosphate derivative and the amine have been reacted in an equimolar amount to form the composition. The amine has a molecular weight of 2,225 Da, a nitrogen content of 1.22 wt. %, and is commercially available from Infineum USA L.P. No additional components have been added.

Referring to Table I, each of the Example "A" compositions includes 50 ppm phosphorus imparted by the dithiophosphate derivative. The ditridecyl amine does not hurt pump performance. However, the polyamine does hurt pump performance. It is thought that the polyamine could be suspending the dithiophosphate derivative in solution thereby not allowing the antiwear compound to reach the surface of the composition.

TABLE II

| Thermal Stability | Example No. | | |
|---|---|---|---|
| (ASTM D2070) | 1B | 2B | 3B |
| Total sludge (mg/100 mL)* | 47.7 | 24.9 | 5.8 |
| *comment | Fail | Moderate | Pass |

Referring to Table II, each of the Example "B" compositions are the same as the corresponding Example "A" compositions. However, each of the Example "B" compositions includes 500 ppm phosphorus imparted by the dithiophosphate derivative (rather than 50 ppm). It is thought that utilizing 50 ppm of phosphorous makes passage of the pump tests challenging, while utilizing 500 ppm of phosphorous makes passage of sludge tests challenging. The ditridecyl amine helps in sludge. It is thought that the ditridecyl amine could be acting as a dispersant. It is thought that the polyamine is most likely dispersing sludge.

TABLE III

| Turbine Oil Stability Test | Example No. | | |
|---|---|---|---|
| (TOST) Sludge (ASTM D4310) | 1B | 2B | 3B |
| Total sludge (mg)* | 805.61 | 6325.95 | Solid/Fail |
| *comment | Fail | Fail | Fail |
| Dissolved copper in oil/heptane layer (ppm)** | 7 | 4 | 225 |
| **comment | Pass | Pass | Fail |

Referring to Table III, the ditridecyl amine is bad for TOST sludge, but the polyamine is worse. As for copper dissolution, it is thought that the polyamine is attacking the copper catalyst.

TABLE IV

| Zinc Compatibility | Example No. | | |
|---|---|---|---|
| (based on AFNOR NF E 48-693) | 1B | 2B | 3B |
| Appearance* | hazy | clear and bright | clear and bright |
| Filtration index* | Fail | 1.34 | 1.06 |
| *comment | Fail | Pass | Pass |

Referring to Table IV, both amines help with zinc compatibility Zinc compatibility is assessed by filtration indices and the test is based on AFNOR NF E 48-693. The calculation gives an indication of compatibility by dividing the time to filter the last 100 mL of oil by the first 50 mL of oil (which is multiplied by 2 to give a proper ratio). If the filtration index is >1 then it can be concluded that the filter is being blocked by insolubles and the formulation is not zinc compatible. If the filtration index is 1 then the oil is deemed perfectly compatible.

Usually "good" oils will be less than 1.5 and "bad" oils with be greater than 2. For zinc compatibility, 330 mL of oil is blended in a kitchen blender for 5 minutes at 1500 rpm and then stored at 100° C. for 7 days followed by 1 day at room temperature. A typical zinc test oil is 90% of the candidate oil, in this case 500 ppm P hydraulic formulations and 10% of a contaminant oil prepared from 0.85% HiTEC® 521 Antiwear Hydraulic Additive Package (428 ppm zinc) which equates to 43 ppm zinc contamination in the test fluid. HiTEC® 521 Antiwear Hydraulic Additive Package is commercially available from Afton Chemical of Richmond, Va.

Gas chromatography (GC) is used to perform a headspace analysis on samples of Example 1 (neat dithiophosphate derivative) and Example 2 (dithiophosphate derivative neutralized with ditridecyl amine). The GC procedure used is set forth in ASTM D5504. To start, "original" samples are prepared by adding the respective composition to headspace vials, and "aged" samples are prepared by adding the composition to headspace vials and aging each headspace vial with the composition therein for 72 hours at 60° C. Each individual original and aged sample is injected through a 6 port gas sampling valve on an Agilent 7890 GC and tested in accordance with ASTM D5504. The processing parameters are as follows:

Oven Temperatures:
    a. Initial Temperature: 35° C. for 5 minutes
    b. Ramp Rate 1: 10° C./min to 100° C.
    c. Ramp Rate 2: 20° C./min to 275° C. and hold for 25 minutes Column Specifications:
    a. JW Scientific DB-1 105 m×0.53 mm×5.00 microns
    b. Operating Temperatures: −60° C. to 260° C./280° C.
    c. Antek 7090S Detector
    d. Serial Number US47890214

$H_2S$ generation in PPM is then calculated based upon an internal standard. The invention compositions each have far less than 10 ppm $H_2S$. In addition, the invention compositions have increased thermal stability relative to the comparative compositions.

Referring now to Table V below, Headspace Analysis of Original and Aged samples of Examples 1 and 2 are set forth.

TABLE V

| | PPM Hydrogen Sulfide ($H_2S$) | PPM Carbonyl Sulfide (COS) | PPM Carbon Disulfide ($CS_2$) |
|---|---|---|---|
| Original Samples (No Aging) | | | |
| Original Example 1 | 1 | 2.6 | 2 |
| Original Example 2 | 0.1 | 0.15 | 0.1 |
| Aged Samples (72 hours at 60° C.) | | | |
| Aged Example 1 | 11.3 | 3 | 2 |
| Aged Example 2 | 0.15 | 1.2 | 0.15 |

Referring now to Table VI below, the $H_2S$ generation of samples of Example 1 aged for, 30, 40, 50, and 60, ° C. for 72 hours are set forth.

TABLE VI

| | Hydrogen Sulfide ($H_2S$) | Carbonyl Sulfide (COS) | Carbon Disulfide ($CS_2$) |
|---|---|---|---|
| Original Example 1 (30° C.) | 0.5 | 2.4 | 2.7 |
| Example 1 for 72 hours at 30° C. | 1.0 | 3.4 | 3.1 |
| Original Example 1 (40° C.) | 1 | 2.7 | 2.8 |
| Example 1 for 72 hours at 40° C. | 2.2 | 3.3 | 2.9 |
| Original Example 1 (50° C.) | 1 | 2.7 | 2.8 |
| Example 1 for 72 hours at 50° C. | 7.2 | 5.8 | 2.5 |
| Original Example 1 (60° C.) | 1 | 2.6 | 2 |
| Example 1 for 72 hours at 60° C. | 11.3 | 3 | 2 |

As is shown in Tables V and VI, the neat dithiophosphate derivative of Example 1 generates significant amounts of free $H_2S$, COS, and $CS_2$ upon aging. In contrast, referring now to Table V, the dithiophosphate derivative neutralized with ditridecyl amine of Example 2 generates significantly less free $H_2S$, COS, and $CS_2$ upon aging than the neat dithiophosphate derivative of Example 1.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A composition comprising:
   a reaction product of:
   a dithiophosphate derivative of general formula (I):

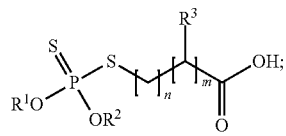

wherein $R^1$ and $R^2$ independently of one another are $C_3$-$C_{18}$ alkyl, $C_5$-$C_{12}$ cycloalkyl, $C_5$-$C_6$ cycloalkylmethyl, $C_9$-$C_{10}$ bicycloalkylmethyl, $C_9$-$C_{10}$ tricycloalkylmethyl, phenyl, or $C_7$-$C_{24}$ alkylphenyl, alternatively $R^1$ and $R^2$ together are $(CH_3)_2C(CH_2)_2$; $R^3$ is hydrogen or methyl; and the sum of n+m is at least 1, and a ditridecyl amine;
   wherein the reaction product comprises an amine salt and is present in an amount of at least about 25 wt. %.

2. The composition as set forth in claim 1, wherein the reaction product is present in an amount of at least about 50 wt. %.

3. The composition as set forth in claim 1, wherein the reaction product is present in an amount of at least about 75 wt. %.

4. The composition as set forth in claim 1, wherein $R^1$ and $R^2$ independently of one another are $C_3$-$C_{18}$ alkyl, $C_5$-$C_6$ cycloalkyl, or $C_7$-$C_{18}$ alkylphenyl.

5. The composition as set forth in claim 1, wherein $R^3$ is hydrogen and the sum of n+m is from 1 to 25.

6. The composition as set forth in claim 1, wherein said dithiophosphate derivative is β-dithiophosphorylated propionic acid.

7. The composition as set forth in claim 1, further comprising free dithiophosphate derivative.

8. The composition as set forth in claim 1, meeting Occupational Safety & Health Administration (OSHA) Standard 29 CFR 1910.1000, TABLE Z-2 for hydrogen sulfide ($H_2S$) exposure which requires that exposures not exceed 20 parts per million (ppm) subject to an exception that if no other measurable exposure occurs during an 8-hour work shift, exposures may exceed 20 ppm, but not more than 50 ppm, for a single time period up to 10 minutes.

9. The composition as set forth in claim 1 as an antiwear additive.

10. A method of forming the composition as set forth in claim 1, said method comprising a step of combining the dithiophosphate derivative and the ditridecyl amine to form the composition.

11. A method of increasing thermal stability of a dithiophosphate derivative that decomposes to form hydrogen sulfide ($H_2S$), said method comprising a step of combining a dithiophosphate derivative of general formula (I):

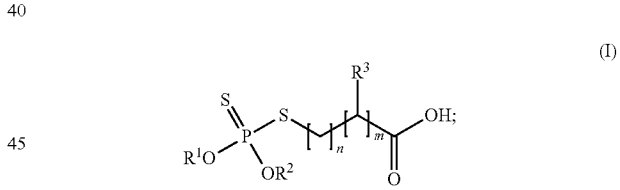

wherein $R^1$ and $R^2$ independently of one another are $C_3$-$C_{18}$ alkyl, $C_5$-$C_{12}$ cycloalkyl, $C_5$-$C_6$ cycloalkylmethyl, $C_9$-$C_{10}$ bicycloalkylmethyl, $C_9$-$C_{10}$ tricycloalkylmethyl, phenyl, or $C_7$-$C_{24}$ alkylphenyl, alternatively $R^1$ and $R^2$ together are $(CH_3)_2C(CH_2)_2$; $R^3$ is hydrogen or methyl; and the sum of n+m is at least 1, and
   a ditridecyl amine;
   wherein the ditridecyl amine substantially prevents thermal decomposition of the dithiophosphate derivative.

12. The method as set forth in claim 10, wherein a decomposition temperature of the dithiophosphate derivative is at least about 60° C.

13. The method as set forth in claim 10, wherein after the step of combining, $H_2S$ exposure from the dithiophosphate derivative does not exceed 10 ppm (15 mg/m3).

* * * * *